United States Patent
Zamfes

(12) 
(10) Patent No.: US 6,301,953 B1
(45) Date of Patent: Oct. 16, 2001

(54) QUANTIFICATION OF DRILLING MUD CUTTINGS CHARACTERISTICS AS A MEASURE OF RELATIVE PERMEABILITY

(76) Inventor: Konstandinos S. Zamfes, 1830 - 10$^{th}$ Avenue SW., Calgary, Alberta (CA), T3C 0J8

( * ) Notice: Subject to any disclaimer, the term of this patent is extended or adjusted under 35 U.S.C. 154(b) by 0 days.

(21) Appl. No.: 09/461,020

(22) Filed: Dec. 15, 1999

(30) Foreign Application Priority Data

Dec. 16, 1998 (CA) .................................................. 2256255

(51) Int. Cl.$^7$ .................................................. G01N 15/08
(52) U.S. Cl. ........................................... 73/38; 73/152.04
(58) Field of Search ..................................... 73/38, 152.04, 73/152.05, 152.25

(56) References Cited

U.S. PATENT DOCUMENTS 5,205,164 * 4/1993 Steiger et al. .................... 73/152.11
5,285,692 * 2/1994 Steiger et al. .................... 73/866
5,844,136 * 12/1998 Marsala et al. ...................... 73/38

* cited by examiner

Primary Examiner—Hezron Williams
Assistant Examiner—Jay L. Politzer
(74) Attorney, Agent, or Firm—Sean W. Goodwin

(57) ABSTRACT

A method is provided for establishing semi-quantitative values indicative of porosity and permeability of a formation during drilling. A sample of mud is analyzed and the proportions of each grain constituents are classified into their respective grain size divisions. Each proportion is multiplied against a corresponding weighting factor for establishing values representative of the relative contribution to the formation's porosity and when summed they establishing numeric values corresponding to an environmental index related to the porosity of the formation. Through the assignment of values for ranges of other conventional qualitative characteristics, similar and useful semi-quantitative value of relative permeability can be determined which is proportional to the environmental index, grain angularity, extent of sorting, porosity and is inversely proportional to the extent of cementation.

14 Claims, 2 Drawing Sheets

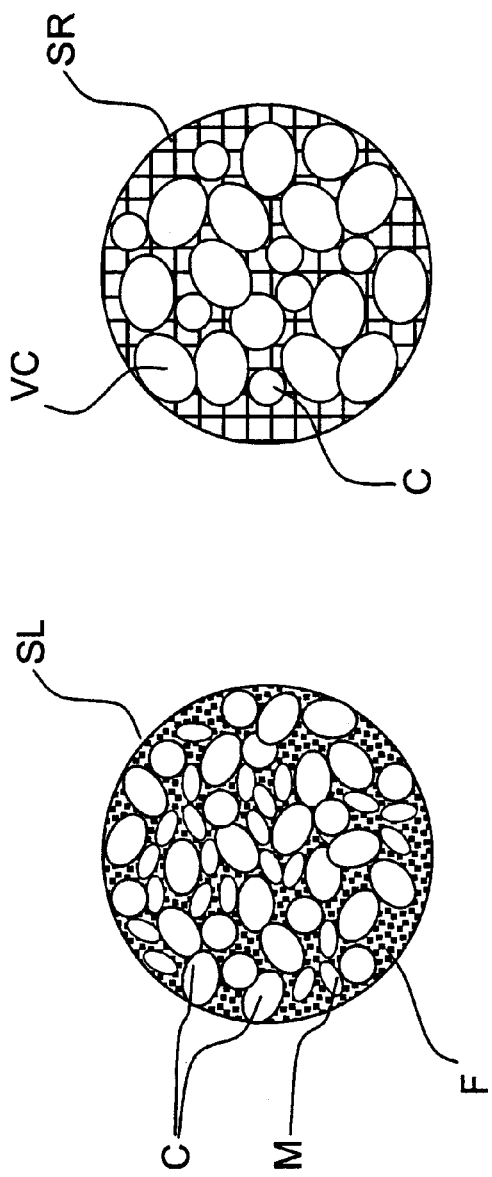

QUANTIFICATION OF DRILLING MUD CUTTINGS CHARACTERISTICS AS A MEASURE OF RELATIVE PERMEABILITY

FIELD OF THE INVENTION

This invention relates to substantially real-time field analysis of drilling mud cuttings for determining the permeability of the formations through which drilling has occurred in order to assess zones for potential of hydrocarbon production.

BACKGROUND OF THE INVENTION

One of the challenges during drilling is to identify zones of interest in the formation. Zones of interest are usually distinguished by their permeability relative to the entire formation through which the drilling is occurring. Zones of high permeability contain highly porous rock, having interconnections between the pores, which allow the hydrocarbons residing within the rock to flow through and out of the rock. Suitable reservoir rock is therefore porous, permeable and contains sufficient hydrocarbon to make it economically feasible to drill and produce them.

Ideally, the identification of zones of interest should occur at the time of drilling, so as to be most efficient and cost effective, however most methods of determining permeability are rarely determined while drilling.

One prior art method is to perform a drill stem step in which the drill bit is tripped out, a tool is run in and pressure over time is monitored. Dril stem tests, while usually effective and time consuming and expensive. Others apply qualitative geological analysis of the drilling mud cuttings for a tough yet often very inaccurate assessment of the formation characteristics.

It is known to pump drilling mud downhole through the drill string to the bit to flush cuttings and hydrocarbons from around the bit. The mud is flowed up the annulus between the wellbore and the drilling string, to the surface for removal of solids and cuttings in an active mud system. The recovered mud, containing the cuttings, is flowed across a shale shaker where large solids are removed and can be sampled. A mud tank containing cleaning systems, such as sumps or centrifuges, are used to remove the fine particulates. The cleaned mud can then be recirculated downhole.

The solids in the mud returning from the wellbore are representative of the formation and can be analyzed for a number of characteristics indicative of it's hydrocarbon producing ability.

Some quantitative values for drilling have already available through observation of drilling performance, including such parameters as force of the bit (FOB) and bit revolutions per minute (RPM). Drilling through highly porous and possibly permeable rock results in an increased RPM and a decrease in the FOB. Additionally, the rate of penetration (ROP) is determined and is much faster through porous rock. Other methods and equipment exist for the measurement of hydrocarbon content in porous and permeable rock and require sophisticated on-site equipment and monitoring devices.

In its simplest form, conventional analysis has been performed qualitatively, largely by visually assessing characteristics known to occur in suitable reservoir rock. Such characteristics include the size of particles present, the angularity of the particles, the degree to which the particle sizes are similar (sorting), the degree to which the particles bind together (cementation), and the porosity of the rock and have been individually assessed by many different means. Industry standards have been set for these qualitative analyses, however they remain, to a large degree, subjective.

As sampling is normally done at defined drilling depths, characteristics can be indexed to the drilling depth using the lag time required to bring the mud to the surface. The zones of interest can then be identified on well logs coordinated with the depth and lithology of the sample.

Because of the subjective nature of visual analysis, even though attempts have been made to set standards, it would be advantageous to provide an easily calculated quantitative or semi-quantitative index that utilizes all of the simply assessed characteristics of the cuttings to determine a relative index of permeability.

SUMMARY OF THE INVENTION

Applicant has determined that conventional analysis of drilled cuttings can be rendered or transformed from the merely qualitative (e.g. coarse) to a semi-quantitative (Index=23) values through application of the method of the invention. In one preferred aspect of the invention, and in contradistinction to the prior art which takes visual analysis of a cuttings sample and applies a statement of its quality, a quantitative grain size analysis is implemented to apply a more representative semi-quantitative assessment of a cuttings sample's of grain size.

In a broad aspect, a method of quantitating relative porosity of a drilled formation from a cuttings sample is performed, the sample having constituents which may be classified into plurality of discrete grain size divisions, and comprising the steps of:

assigning numerical weighting factors to each of the discrete grain size divisions having larger values for larger grain sizes, preferably in the range of 1–5;

classifying the proportions of the cuttings' constituents between the discrete grain size divisions, preferably totaling 10;

multiplying the classified proportions by the corresponding weighting factor for establishing values representative of the relative contribution to the formation's porosity; and summing the relative contributions for each grain size division for establishing numeric values corresponding to the porosity of the formation.

Applicant has determined that other conventional qualitative characteristics of a cuttings sample can be advantageously combined for transforming them into a more useful semi-quantitative value of relative permeability. Such additional characteristics include angularity, sorting, cementation and porosity. Accordingly, in another aspect of the invention, a method is provided for quantitating relative permeability of a drilled formation comprising the steps of:

assigning numerical values for the proportion grains in each of a plurality of grain size divisions within a sample and a weighting factor for each division corresponding thereto for establishing a environmental index value EnviroNdx;

assigning a numerical value to the degree of angularity of grains within a sample for establishing an angularity index value AngNdx;

assigning a numerical value to the degree to which the grains within a sample are the same for establishing a sorting index value SrtNdx;

assigning a numerical value to the degree to which the grains within a sample bind together for establishing a cementation index value CemNdx;

assigning a numerical value to the degree of porosity of the sample for establishing a porosity value Por; and determining the relative permeability index PermNdx of the sample as being substantially proportional to EnvNdx, AngNd, SrtNdx and Por and inversely proportional to CemNdx.

Most preferably the relationship is as follows:

$$PermNdx = \frac{EnvNdx \times (AngNdx)^2 \times (SrtNdx)^2}{(CemNdx)^2} \times Por.$$

BRIEF DESCRIPTION OF THE DRAWINGS

FIG. 2 is a schematic representation of two mud samples being assessed a permeability rating by the qualitative prior art method and through application of an embodiment of the present invention.

DETAILED DESCRIPTION OF THE PREFERRED EMBODIMENT

Figure 1:
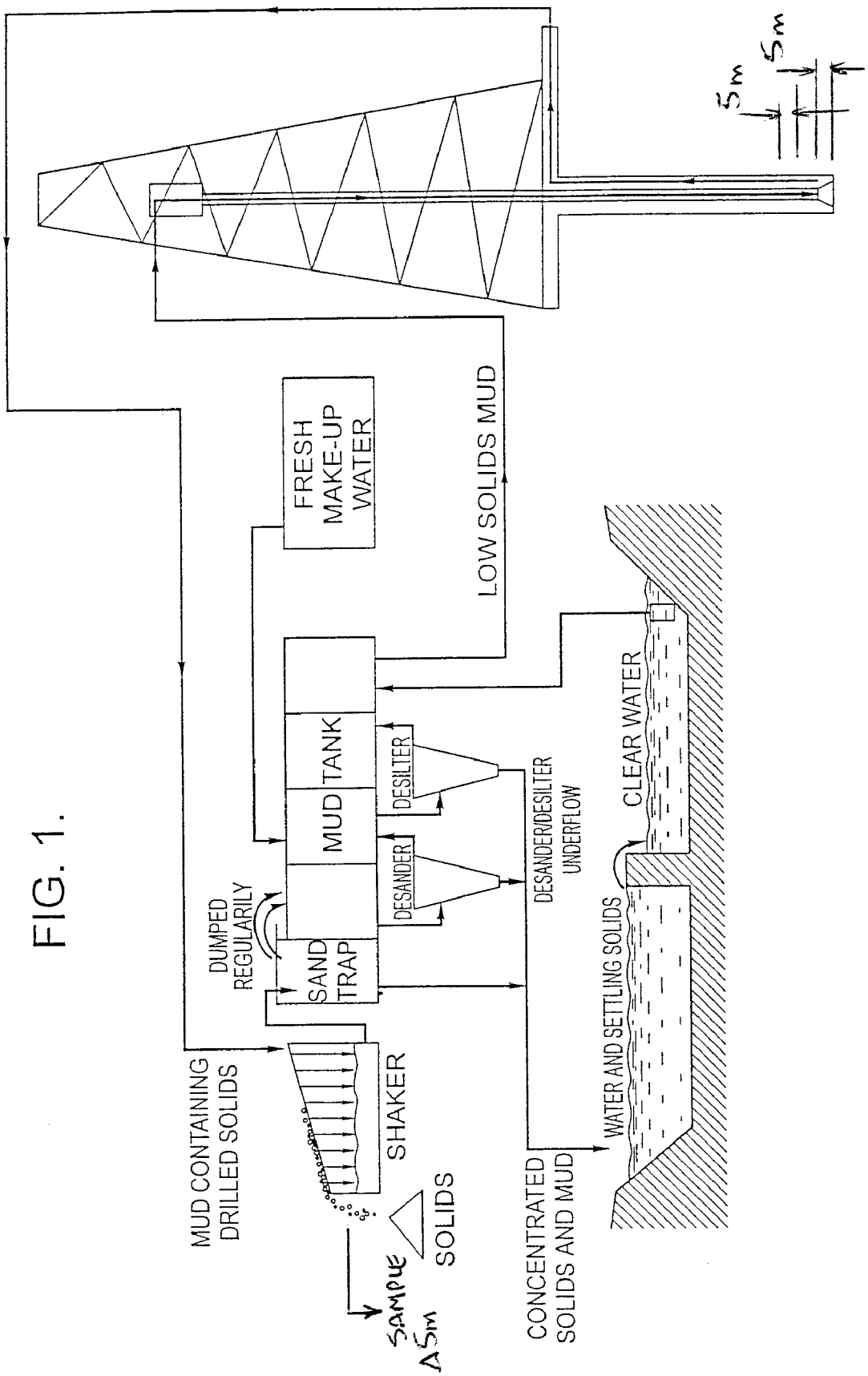
FIG. 1 is a schematic illustrating an active mud circulating system with a mud sample being obtained from the shale shaker.

Having reference to FIG. 1, drilling mud is pumped downhole through a drilling string to flush cuttings and hydrocarbons from around the drill bit. Solids laden mud is flowed up the annulus between the wellbore and the drilling string and is flowed across a shale shaker, to remove large solids. The reminder of the drilling mud is deposited into a mud tank where fine particulates are removed by mechanisms such sumps, centrifugation or a combination thereof. The cleaned or low solids containing mud is then reconstituted and recycled back to the drilling rig use downhole.

Cuttings are sampled from the shale shaker at predetermined intervals, indexed to every 5 meters of drilling depth, correlated to the formation being drilled by the lag time required to bring the mud to the surface.

The cuttings are washed and visually assessed for a number of characteristics normally found in suitable reservoir rock.

Grain Size—Environmental Index (EnvNdx)

Traditionally, the constituents of cuttings are assessed on their grain size. Grains size is rated on a scale from very fine to very coarse, with a formation which is formed of very fine grains being less permeable than one formed of very coarse grains.

Further, the grain size can be interpreted as being representative of the potential energy of the sample, assessed from the source as being the highest energy. The coarser the material, the closest to the source and the higher the energy. This kind of analysis is useful when assessing where one may drill next.

One method of determining the grain size is to visually inspect the results after allowing the sample to settle in a cylinder filled with water. The solids are typically graded into discrete divisions according to the size ranges show in Table I. These grades or divisions are sometimes known as the "Wentworth Scale" wherein the maximum size in for each division is double that for the previous division.

TABLE I

| Grade | Abbrev. | Minimum mm | Maximum mm |
| --- | --- | --- | --- |
| Very Fine (Silt) | VF | 0.004 | 0.0625 |
| Fine (Very Fine) | F | 0.0625 | 0.125 |
| Medium (Fine) | M | 0.125 | 0.250 |
| Coarse (Medium) | C | 0.250 | 0.500 |
| Very Coarse (Coarse) | VC | 0.500 | 1.000 |

The problem with the prior art qualitative approach is that this assessment permits a geologist to make only a single assessment; be it Medium (M) or Fine (F). Samples are rarely one or the other but are a combination of grain sizes. Conventionally, a geologist may attempt to average the sample visually.

For the purposes of this invention's quantitation, each sample is assumed to have an arbitrary total grain grading score of ten (10), representative of 100 percent of the individual proportions of each of the five grades listed in Table I. It is also recognized that coarser size grains have a greater deemed energy, related also to a positive impact on porosity and permeability and thus are weighted more heavily. Accordingly, the grain grade of a sample is assessed an increasing weighting system as the grain grade shifts from fine to coarse, demonstrated herein as a linearly increasing yet arbitrary value of one (1) to five (5), with 1 being very fine and 5 being very coarse, indicative of increasing permeability associated with increasing coarseness.

Analytical techniques have long been known for assessing populations in a sample and such techniques can be used to place quite accurate percentages of the fraction of size in the sample. Thus, if a sample is assessed of graded as having 20% Fine (grain grade of 0.2) and 80% Coarse grains (grain grade of 8 for a total of 10), with none of the other grades present, an index (the "Environmental Index" of "Env. Index" for short) can be calculated by multiplying the assessed percentage for each grain by its corresponding weighting factor and then summing the totals as follows:

|  | V | F | M | C | VC |  |  |
| --- | --- | --- | --- | --- | --- | --- | --- |
| Grain grade | 0 | 2 | 0 | 8 | 0 |  |  |
| Weighting 1 | 2 | 3 | 4 | 5 |  |  |  |
| Environmental Index | 0 | 4 | 0 | 32 | 0 | = | 36 |

Conversely, if a sample has 80% Fine (grain grade of 8) and 20% Coarse grains (grain grade of 2), without any of the other grades present, the resulting Environmental Index is determined as follows:

|  | V | F | M | C | VC |  |  |
| --- | --- | --- | --- | --- | --- | --- | --- |
| Grain grade | 0 | 8 | 0 | 2 | 0 |  |  |
| Weighting 1 | 2 | 3 | 4 | 5 |  |  |  |
| Environmental Index | 0 | 16 | 0 | 8 | 0 | = | 24 |

The above examples illustrate a numerical and semi-quantitative indication of permeability of the sample, having an Env. Index of 36 being deemed more permeable that one having an Env. Index of 24.

Having reference to FIG. 2, two samples SL,SR are illustrated which are a combination of different grain grades.

The left sample SL has a lot of fine material F, some medium M and maybe a little coarse C. The right sample SR is primarily coarse material C,VC. The grid of the sampling plate is visible through the right sample's coarse grains.

Using the prior art, a wellsite geologist may assess the left sample SL as being an average of Medium grains and mark off well the log sheet for that sample as being M. The same geologist may assess the right sample SR as being basically Coarse and mark or check off the log sheet for that sample as C.

Unfortunately, it is not a fair assessment to rate these two samples SL,SR as being so close in grain grade as Medium M and Coarse C. This is not very representative of the energy of the sample or its relative porosity or permeability.

Using the method of the invention, and referring to Tables F1, F2 for samples SL and SR, five grades are set forth, assigned weighting of 1 through 5. The left sample is inspected to have about 10% VF, 60% F, 20% M and 10% C. Applying the weighting factors, the left sample SL now gets an Env. Index of 23 and the right sample an Env. Index of 42. So, rather than being assessed as being adjacent in a prior art rating system of 1–5 (VF–VC), now the right sample SR is assessed as having twice the potential energy the left sample SL; demonstrating a proportional increase in its potential for permeability.

The invention further assists in avoiding misinterpreting anomalous cuttings, such as in a case where drilling has occurred through a vug in an otherwise porous or permeable formation (a vug being a small cavity in rock lined with crystals). The drilled cuttings are analyzed and unless the analyst recognizes the fine matter portion as being crystals from a vug in a coarse formation then, according to the traditional grain size grading, an analyst would only have a limited choice of grading the sample, likely grading the sample as very fine and improperly indicating low porosity, when the overall formation actually has high porosity. In contradistinction, using the Env. Index, all the grain sizes in the sample would be represented in the calculation and regardless whether crystals are detected, the Coarse grains contribute to grade the sample as having a higher porosity, more indicative of the true nature of the sample.

Thus, an index calculated in this fashion, eliminates the analyst's bias to visually assess only the major constituents of the sample and instead accounts for the sample's entire constituents and relates them to permeability. It provides a numerical value that is easily compared from sample to sample or included in further calculations of relative porosity and permeability.

In even more preferable embodiments of the invention, conventional qualitative characteristics can be similarly quantified.

Angularity Index (AngNdx)

The shape of grains within sedimentary rock is also indicative of its permeability. Angularity of grains within the sample is conventionally rated according to categories outlined in Table 2.

TABLE 2

| Rate | Abbrev. | Description |
| --- | --- | --- |
| Angular | A | sharp and pronounced protrusions |
| Subangular | a | many protrusions somewhat rounded |
| Subrounded | r | rounded, less pronounced protrusions |
| Rounded | R | rounded |

For the purposes of calculation of relative permeability, the categories above are assigned numerical values of 1 through 4 for rating A, a, r and R, respectively. Thus, the more angular a sample, the less permeable it is likely to be and conversely, the less angular, the more permeable.

Sorting Index (SrtNdx)

A sorting rating based on the number of different grain sizes present within the sample is conventionally rated according to categories outlined in Table 3.

TABLE 3

| Rate | Abbrev | Number of size grades |
| --- | --- | --- |
| Well | W | 1 or 2 size grades |
| Medium | M | 3 or 4 size grades |
| Poor | P | 5 or more size grades |

For the purposes of calculation of relative permeability, the categories above are assigned numerical values of 3,2 and 1 for W, M and P respectively. Thus, having fewer size grades within a sample is indicative of greater permeability than having a plurality of varying sizes within a sample.

Cementation Index (CemNdx)

The degree to which grains bind together within a sample is conventionally rated by percentage, as indicated in Table 4.

TABLE 4

| Rate | Percentage |
| --- | --- |
| cm-1 | <10% |
| cm-2 | 10–20% |
| cm-3 | 20–30% |
| cm-4 | 30–40% |
| cm-5 | >40% |

For the purposes of calculation of relative permeability, the categories above are assigned numerical values of 1 through 5 for cm-1 through cm-5, respectively.

Porosity

Porosity is generally graded on a scale of 0–20%, however for the purposes of quantification, this scale has been expanded to 0–40%. The expansion of the scale, wherein the previously graded to 20% is now graded at to 40%, allows for a greater distinction between samples and provides a greater spread of values when used to calculate a permeability index.

Permeability Index (PermNdx)

Permeability has most commonly been assessed by the wellsite geologist based, in part, on a subjective compilation of the aforementioned physical characteristics of cutting samples.

It has been found that combining the indexes in a novel calculation, where permeability is proportional to the environmental index, the square of the angularity index, the square of the solids sorting and to the inverse of the square of the cementation index, a relative permeability index can be calculated.

The permeability index is therefore calculated by the following formula, $$PermNdx = \frac{EnvNdx \times (AngNdx)^2 \times (SrtNdx)^2}{(CemNdx)^2} \times Porosity$$

where:
  PermNdx=permeability index (0–144,000)
  EnvNdx=environmental index (10–50)
  AngNdx=angularity index (1–4)
  SrtNdx=sorting index (3–1)
  CemNdx=cementation index (1–5)
  Porosity=% porosity (0–40%)

What is claimed is:

1. A method of quantitating relative permeability of a drilled formation from cuttings comprising the steps of:
   (a) assigning numerical values for the proportion of grains in each of a plurality of grain size divisions within a sample and a weighting factor for each division corresponding thereto for establishing a environmental index value EnvNdx;
   (b) assigning a numerical value to the degree of angularity of grains within a sample for establishing an angularity index value AngNdx;
   (c) assigning a numerical value to the degree to which the grains within a sample are the same for establishing a sorting index value SrtNdx;
   (d) assigning a numerical value to the degree to which the grains within a sample bind together for establishing a cementation index value CemNdx;
   (e) assigning a numerical value to the degree of porosity of the sample for establishing a porosity value Por; and
   (f) determining the relative permeability index PermNdx of the sample as being substantially proportional to EnvNdx, AngNd, SrtNdx and Por and inversely proportional to, CemNdx.

2. The method as recited in claim 1 wherein the relative permeability index PermNdx of the sample is established using the relationship:

$$PermNdx = \frac{EnvNdx \times (AngNdx)^2 \times (SrtNdx)^2}{(CemNdx)^2} \times Por.$$

3. The method as described in claim 1 wherein the weighting factors for grain size divisions increase linearly with a doubling of the grain size divisions.

4. The method as described in claim 3 wherein grain sizes are classified in five divisions, the value of a classified proportion of each constituent being determined on a scale of 1 to 10 and wherein the corresponding weighting factors have values of 1–5 respectively.

5. The method as described in claim 4 wherein the grain sizes are classified into five divisions having constituent sizes of up to 0.0625 mm, 0.125, 0.25, 0.5 and 1 mm respectively.

6. The method as described in claim 1 wherein the angularity index value increases linearly for grains rated as angular, subangular, subrounded and rounded respectively.

7. The method as described in claim 6 wherein the angularity index values are 1–4 for grains rated as angular, subangular, subrounded and rounded respectively.

8. The method as described in claim 1 wherein the sorting index value decreases for cuttings which are more and more poorly sorted.

9. The method as described in claim 8 wherein the sorting index values are 3,2 and 1 for cuttings which are well, medium and poorly sorted respectively.

10. The method as described in claim 1 wherein the cementation index value increases with an increased degree to which the grains bind together.

11. The method as described in claim 10 wherein the cementation index values are 1–5 for percentages of the degree to which the grains bind together of <10%, 10–12%, 20–30%, 30–40% and >40% respectively.

12. The method as described in claim 1 wherein the porosity values range from 0–40%.

13. The method as recited in claim 1 wherein:
   the EnvNdx is the product of the proportion of each constituent in each of one of five grain size divisions and the corresponding weighting factor, wherein the proportion of each constituent being determined on a scale of 1 to 10, and wherein the corresponding weighting factors have values of 1–5 respectively;
   the AngNdx are 1–4 for grains rated as angular, subangular, subrounded and rounded respectively;
   the SrtNdx are 3,2 and 1 for cuttings which are more well, medium and poorly sorted respectively;
   the CemNdx are 1–5 for percentages of the degree to which the grains bind together of <10%, 10–12%, 20–30%, 30–40% and >40% respectively; and
   the Por range from 0–40%.

14. The method as recited in claim 13 wherein the PermNdx of the sample is established using the relationship:

$$PermNdx = \frac{EnvNdx \times (AngNdx)^2 \times (SrtNdx)^2}{(CemNdx)^2} \times Por.$$

* * * * *